United States Patent [19]

Teipel

[11] Patent Number: 4,486,315
[45] Date of Patent: Dec. 4, 1984

[54] IMMUNOASSAY MICROPARTICLE WASHING SYSTEM AND METHOD OF USE

[75] Inventor: John W. Teipel, Skillman, N.J.

[73] Assignee: Ortho Diagnostic Systems Inc., Raritan, N.J.

[21] Appl. No.: 358,419

[22] Filed: Mar. 11, 1982

[51] Int. Cl.³ .............................................. B01D 21/26
[52] U.S. Cl. ..................................... 210/772; 210/789; 210/518; 210/927; 436/177; 436/807; 422/101
[58] Field of Search ............... 210/787, 927, DIG. 24, 210/516, 517, 518, 789, 772; 436/177, 518, 807; 422/101, 102; 73/61.4

[56] References Cited

U.S. PATENT DOCUMENTS

| | | | |
|---|---|---|---|
| 3,075,694 | 1/1963 | Anderson | 233/40 |
| 3,677,710 | 7/1972 | Hirsch | 210/927 |
| 3,687,296 | 8/1972 | Spinosa et al. | 210/406 |
| 3,799,342 | 3/1974 | Greenspan | 210/DIG. 24 |
| 3,858,795 | 1/1975 | Joyce | 210/927 |
| 3,914,985 | 10/1975 | von Behrens | 73/61.4 |
| 3,932,277 | 1/1976 | McDermott et al. | 210/DIG. 24 |
| 3,935,113 | 1/1976 | Ayres | 210/927 |
| 3,953,172 | 4/1976 | Shapiro et al. | 23/230 R |
| 3,957,653 | 5/1976 | Blecher | 210/518 |
| 3,960,727 | 6/1976 | Hochstrasser | 210/782 |
| 3,962,085 | 6/1976 | Liston et al. | 210/927 |
| 4,035,294 | 7/1977 | Landers et al. | 210/77 |
| 4,158,547 | 6/1979 | Rousseau et al. | 210/927 |
| 4,203,840 | 5/1980 | Stoeppler et al. | 210/787 |
| 4,244,694 | 1/1981 | Farina et al. | 23/230 B |
| 4,308,028 | 12/1981 | Elkins | 23/230 B |

Primary Examiner—Richard V. Fisher
Assistant Examiner—John W. Czaja
Attorney, Agent, or Firm—Geoffrey G. Dellenbaugh; Mark A. Hofer

[57] ABSTRACT

A particle washing system and method of use provides for the placement of the fluid containing the desired particles within an inner tube having near the bottom thereof an orifice plugged with a material for sealing the particulate containing fluid from a wash fluid under forces substantially equal to 1G. The inner tube is positioned within an outer tube which contains a wash fluid having a density at least equal to that of the particle containing solution but less than that of the particles. Application of centrifugal force, substantially greater than 1G, and directed toward the bottom of the outer tube, causes the sealing material to be dislodged thereby permitting the particles to move through the orifice and through the outer solution. Thus the particles are collected from the inner solution, washed by the outer solution, and pelleted at the bottom of the outer tube.

10 Claims, 3 Drawing Figures

U.S. Patent Dec. 4, 1984 4,486,315
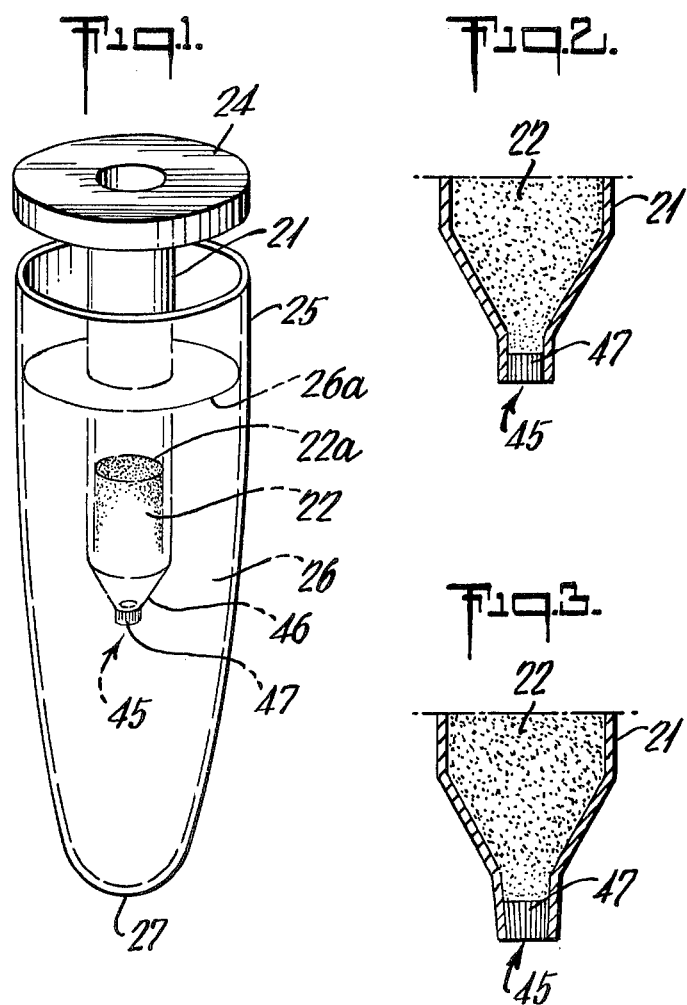

IMMUNOASSAY MICROPARTICLE WASHING SYSTEM AND METHOD OF USE

FIELD OF THE INVENTION

This invention relates to apparatus and methods for the separation, collection and washing of particles contained in a fluid wherein such apparatus and methods are easily adaptable for the handling of blood samples, microparticle containing immunoassays and the like.

BACKGROUND OF THE INVENTION

The necessity and desirability of separating blood samples into their respective component parts, for example the cellular components and plasma, for test purposes and other medical applications has long been recognized. These applications are described in length in commonly assigned patent application Ser. No. 290,267 entitled "Particle Washing System and Method of Use", now U.S. Pat. No. 4,435,293, by Graham et al. That application is fully incorporated herein by reference.

The principles taught by Graham et al. are not limited to hematology type applications but may additonally be employed in immunoassay technology. Immunoassay technology is primarily directed towards the use of serologically specific reactions for the determination of the presence of specified antigens or antibodies, either of which may be called a determinant. Often these assays incorporate solid phase components wherein one of the serological determinants, i.e. either the antigen or the antibody, is coated upon a solid substrate such as a microsphere, red blood cell, or other type of microparticle. Following the serological reaction between the antigen and the specifically reactive antibody, the microparticles may be removed from the suspension along with the antigen antibody complex by centrifugation. Thus, unreacted serological determinants remain in solution and can be easily removed prior to identification and quantification of the extent of serological reaction and thus, in turn, quantification of the presence of the determinant to be identified.

The microparticles may take the form of microspheres which can be produced in various size ranges. The predominant size selected will depend upon the desired sensitivity and type of immunoassay performed. Often, in order to insure thorough mixing of the microparticles and other serological reagents, some form of vigorous agitation is required such as vortexing. It has been found that in these rare instances, the devices taught by Graham et al. employing reduced orifices are not always wholly successful in preventing leakage of the mother solution containing the sample and microparticle-immunoassay reagent through the orifice when mixing or when placed in contact with the outer wash solutions. It is an object of the present invention to provide an improved method for eliminating both premature leakage of the mother solution and unwanted mixing of the mother solution and wash solution in the embodiments of the Graham et al. invention employing capillary type orifices when used in operations requiring a high level of mechanical agitation.

Although there are many other types of separation devices available, typically, they are intented to facilitate recovery of the mother solution portion of the suspension and none is intended to permit the facile collection of microparticles from the mother solution or solve the aforementioned problem encountered in the Graham et al. embodiments employing a small diameter orifice.

For example, U.S. Pat. No. 3,932,277 to McDermott et al., directed to the separation of blood fractions, describes a system of tubes, one insertable into the other, whereby one tube inserts a barrier to separate the serum from the red blood cells after centrifuging in an attempt to prevent the mixing of the cells and the serum during decantation of the serum supernatant. During the insertion of the inner tube whereby the barrier is placed between the aforementioned portions, it is possible to have the serum filtered as it passes into the interior of the inner tube. Thus, this invention is directed towards the recovery of serum and requires great care in the placement of the barrier at the surface of the compacted red blood cell portion so as to avoid inadvertant mixing at that interface. Once in place, the barrier will prevent the removal of the red blood cells upon decantation of the serum. Thus, the barrier defeats a technician interested in working with the red blood cell layer from obtaining that cell layer. The McDermott et al. system additionally fails to provide apparatus or methods useful for immunoassays applications employing microparticles.

Similarly, U.S. Pat. No. 4,035,294 to Landers et al. is directed towards the collection, filtration and removal of the supernate following centrifugation. Landers et al. teach the insertion of an inner tube having a filter mounted at the bottom whereby, with the application of force to the inner tube upon insertion, the supernate is filtered through the membrane and is removably collected in the inner tube. As with the previously described reference, the disclosure of Landers et al. teaches an improved method in the filtration and handling of liquid supernate materials and fails to supply needed apparatus and methodology for a superior handling of separated microparticles from an immunoassay reaction solution, an object of the present invention.

U.S. Pat. No. 4,244,694 to Farina et al. describes the use of a reactor/separator device for use in automated solid phase immunoassays. The described device employs a water impermeable disc capable of supporting immunoabsorbents, immobilized antisera, ion exchange resins and other similar materials for reaction with reagents added to the inner tube upon centrifugation. Following the desired reaction, additional centrifugal forces are applied in order to force the aqueous phase through the filter making it water permeable thus permitting separation of desired components. Farina's invention provides a device wherein centrifugal force is employed for the mixing, transferance and separation of reactants in a reactor cavity separated from the collection chamber by a water impermeable disc. Such a device fails to solve the problems enumerated above, specifically those related to the collection and washing of particles suspended in a solution where a minimum of steps and a maximization of economy is desired.

Although the collection of microparticles from an immunoassay reaction solution has been described, it is to be understood that this is by way of illustration and that some of the conventional procedures described as well as the present invention are equally applicable to the separation of particles in general from a mother solution by application of gravitational forces.

It is an object of the present invention to permit the rapid separation and washing of microparticles from a solution in a "one step" operation. It is a further object that the present invention be capable of withstanding physical agitation during an immunoassay reaction without mixing of the reaction solution with the wash solutions. It is another object that during separation of the particles from the solution containing the particles, the particles are washed so as to remove any nonspecific serum coating and to dilute any solute drag. It is yet another object that the original particle containing sample solution be separately maintained from the sedimented particles to permit the facile removal of the original sample solution in order to reduce contamination. It is still another objective of the present invention that these objectives be accomplished in a simple system capable of economical production and employable within simple, inexpensive centrifuges commonly available. It is a further objective of the present invention to not only provide devices but also methodology capable of meeting the desired objectives. These and other objectives will readily become apparent to those skilled in the art in light of the teachings set forth herein.

SUMMARY OF THE INVENTION

In accordance with the principles and objectives of the present invention, there is provided an apparatus which consists of an inner hollow, open-ended tube placed within an outer test tube containing a wash solution. The inner tube additionally has, compared to the diameter of the innertube, a reduced diameter orifice disposed at a position intermediate between the bottom of the outer test tube and the level of the wash solution.

Preferably, the wash solution is chosen to have a density less than that of the particles to be separated but more than that of the sample solution containing the particles so as to minimize mixing between the two solutions during centrifugation. Consequently, for the systems provided, the wash solution or second fluid has at least one component for adjusting the density of said second fluid selected from the group consisting of sodium chloride, glycine, sugars, serum albumin, natural polymers, natural copolymers, synthetic polymers, synthetic copolymers, dextran and Ficoll TM. Ficoll TM is a Pharmacia brand name of a product which comprises neutral polymers of sucrose typically having a molecular weight of 5,000 or more. The serum albumin may be selected from the group consisting of animal serum albumin and human serum albumin. Serum albumin, to be compatible, cannot have human gamma globulin or human complement which would otherwise interfere with immunoassay reactions.

In order to withstand physical agitation and prevent both leakage and premature mixing of the mother solution with the wash solution, the reduced diameter or capillary orifice is sealed by drying within the capillary opening a suspension or solution of either latex, polystyrene latex, polystyrene-butadiene latex, or other synthetic film-forming material, a protein such as albumin, gelatin, fibrinogen and the like, or synthetic or natural soluble polymers such as PVP, dextran, etc. The capillary orifice is filled with such solutions in a quantitative and reproducible manner by touching the tip of the capillary to the solution and allowing it to fill by capillary action. These materials, when dried, should form either a nonsoluble seal within the capillary or a slowly dissolving seal within the capillary. The term solubility is employed here to describe a material which is either soluble in a substance employed in the sample-immunoassay reaction mixture, or in the wash solution. Slightly soluble means it is only slowly soluble such that the time constant for the solubility is much longer than that of the incubation, reaction and/or wash times required. The level of the wash solution is preferably adjusted so that it is greater than the level of the sample solution when the device is assembled, i.e. following the insertion of the inner tube into the outer test tube and the addition of all solutions. With the fluid levels so adjusted, the application of centrifugal force via a centrifuge results in a net upward force on the capillary barrier plug dislodging or rupturing it thereby destroying its sealing capacity.

Following the dislocation of the barrier or plug material and with the continued application of centrifugal force, the particles contained within the mother or sample solution are forced to move through the mother solution, through the orifice and towards the bottom of the outer tube in accordance with the sedimentation coefficients or Svedberg Units characterizing the particles.

The effective application of centrifugal force will ultimately result in pellitization of the desired particles at the bottom of the outer tube. Decantation of the overlying fluid, is then effected by either of two methods. Firstly, the remaining mother-sample solution can be aspirated from the interior of the inner tube followed by extrication of the tube or the mother-sample solution may be removed with the inner tube after the top has been sealed off, i.e. by a finger, and then the washing solution decanted; or secondly, and more simply, the mother-sample solution, inner tube, and outer wash solution can be removed in one decantation step simply by inverting the outer tube. Such a total decantation is preferably performed carefully to avoid significant disturbance of the pellet.

BRIEF DESCRIPTION OF THE DRAWINGS

The objectives and principles of the invention and the preferred embodiments thereof will best be understood by reference to the accompanying drawings wherein.

FIG. 1 is a side view of the particle washing and collecting sysem following insertion of the inner tube into the outer tube.

FIG. 2 is an expanded side view of the bottom of the inner tube of the particle washing and collecting system of FIG. 1.

FIG. 3 is an expanded side view of the preferred embodiment of the bottom of the inner tube of the particle washing and collecting system of FIG. 1.

BEST MODE FOR CARRYING OUT THE INVENTION

The present invention describes a method and device for permitting the separation and collection of particles such as microparticles from a fluid so that during separation, the particles are washed of any contaminants from the mother or immunoassay sample solution. Further, the invention will permit the removal of the mother solution remaining after separation of the particles, i.e. the supernatant, with a minimal of mixing and resulting contamination between the supernatant and the desired particles.

FIG. 1 illustrates an embodiment of such a device showing an inner tube 21 wherein the mother or immunoassay sample solution 22, containing the particles to be separated, is placed. The inner tube 21 preferably has a larger diameter portion 24 at the top of the tube such that after insertion within the outer tube or receptacle means 25, the larger diameter section 24 prevents further insertion of the inner tube 21 into outer tube 25. Such an expanded diameter additionally provides a grasping surface for facilitating removal of the inner tube following centrifugation. Alternate means for supporting the inner tube are described in U.S. Application Ser. No. 290,267 (now U.S. Pat. No. 4,435,293). It is noted that the support feature is not a necessary component of the operational device and may be selected in accordance with user preference.

Inner tube 21 further incorporates at the bottom of the tube an orifice of reduced diameter 45 preferably less than 0.02" in diameter. Orifice 45 will advantageously be located in tube 21 and the slope of walls 46 leading to the orifice adjusted so that substantially all particles will pass through the orifice even if the force applied is not precisely aligned with the central longitudinal axis of inner tube 21. Such a situation would occur, for example, if the invention were placed in a centrifuge having a rotor which did not permit a full 90° movement of test tube 25 during rotation of the rotor.

Orifice 45 is sealed with a plug or barrier means 47 made by drying within the orifice a suspension or solution of latex or other synthetic film-forming material, or a protein such as albumin, gelatin, fibrinogen and the like, or a synthetic or natural polymer such as PVP, dextran and the like. This plug, under normal gravity, should preferably have sufficient strength to maintain sealing integrity during filling, incubation and/or agitation such as vortexing or other conditions appropriate to permit an immunological reaction. Upon the application of centrifugal force of substantially more than 1G, i.e. such as in the neighborhood of 500G's or more conventionally employed to sediment microspheres, the plug, or barrier means will become dislodged or ruptured within the orifice 45. This occurs because the net initial force will be upward in order to equalize the head pressures of the wash solution 26A and the mother solution 22A. Thereafter, the particles responding to the centrifugal force can move through the orifice, the wash solution, and pelletize on the bottom of outer tube 25.

FIG. 2 shows one embodiment wherein the sides of the orifice 45 are essentially parallel and is thus sealed by a cylindrical type plug. FIG. 3 shows the preferred embodiment wherein the sides of the orifice 45 are sloping. Such an orifice would be sealed by a substantially conically shaped plug which, with the application of substantial centrifugal force will become dislodged as described previously. Upon close examination, it can be seen that the plug essentially tumbles in location during centrifugation.

Wash solution 26 is preferably chosen to have a density greater than that of mother solution 22 but not more than that of the particles and additionally, must be compatible with the particles to be separated. For example, if the particles are microspheres coated with immunologically reactive antigens or antibodies, compatibility in the sense used means that the outer wash solution can not alter the microsphere characteristics or interfere with the immunoassay's serological or immunological reactions. The greater density of the surrounding outer wash solution 26 acts to diminish the flow of the inner mother solution 22 into the wash solution during centrifugation and thereby substantially reduce contamination of outer wash solution 26. It is to be understood that these considerations apply generally to all embodiments.

With further reference to FIG. 1, following insertion of the inner tube 21 into outer tube 25 to the extent permitted by increased diameter 24 on inner tube 21, the outer wash solution 26 is preferably displaced by inner tube 21, sealed by plug 47, such that the surface of wash solution 26 rises to a level above that of inner solution 22 before the pressures equalize. Such an arrangement of surface levels is preferred so as to further restrict the sample solution from mixing with the outer wash solution since the interface between these two solutions following dislocation of the barrier means 47 during centrifugation will be contained within inner tube 21. The particle washing device as depicted in FIG. 1 is now ready for centrifugation whereupon force, directed toward point 27, will be exerted upon the particles contained within sample solution 22 to cause them to move through orifice 45, past dislodged barrier 47, and subsequently through wash solution 26 to the bottom 27 of outer tube 25. As the particles pass through wash solution 26, any contaminants occasioned by solute drag or nonspecifically attached to or on the surface of the particle will be removed.

Centrifugal forces are chosen large enough so as to dislodge the barrier 47 and to cause the movement of the particles and a resultant packing or sedimentation at point 27 in the outer tube 25 but not so great as to result in damage to the particles. The distance between barrier means 47 and sedimentation point 27 is advantageously chosen so as to maximize the washing of the particles to be separated from mother solution 22 yet still allow a minimum time for separation. Further, the volume of wash solution 26 is ideally chosen so as to result in a great dilution of any contaminants that escape the mother solution. Naturally, the effectiveness of this embodiment will be greatly reduced if the particles are permitted to agglutinate and form complexes which are larger than the diameter of orifice 45 thereby impeding their passage and ultimate sedimentation.

To accomplish the desired objective of minimal contamination due to physical mixing of the separated particles and the mother solution after centrifugation, an orifice of small diameter is employed in the channel communicating between the mother solution and the outer solution. This small orifice serves to stabilize the two fluids and to minimize mixing due to convection, counter-currents due to density gradients or other currents induced by physical movement of inner tube 21 with relation to outer fluid 26. Additionally, the orifice diameter is preferably chosen so as to permit the formation of an appropriate plug and upon its dislocation, to allow movement of the particles through the orifice yet minimize the amount of mixing between the inner solution 22 and the outer solution 26. It will be apparent to those skilled in this field that these effects can be created by a variety of orifice and plug material combinations and these combinations are intended to be included with the embodiments described herein.

Following centrifugation and the resultant sedimentation of the particles, the inner tube containing the remaining sample solution supernate and the dislodged barrier means is preferably removed in a fashion to minimize physical agitation of the outer solution and thus resuspension of the sedimented particles. An advantage provided by the inner tube is that it permits facile removal of the mother solution along with the walls of the container coated by the mother solution. Thus, by removing the inner tube, this potential source of contamination is quickly and efficiently eliminated thereby preventing contamination of the particles when they are resuspended. The outer solution, in a position atop the sedimented particles, can be removed by techniques well known in the art such as decantation, siphoning and the like.

Inner tube 24 is advantageously constructed of a plastic material such as polyethylene, polystyrene or polypropylene. Outer tube 25 may be constructed of the same materials but advantageously will be a standard glass test tube since these may be purchased economically in bulk quantities and accomodate most commercially obtainable inexpensive centrifuges.

It will be apparent to the skilled worker in this field that various modifications and embodiments of this invention can be made without departing from the spirit and the scope thereof.

What is claimed is:

1. A method of washing and collecting particles contained in a first fluid comprising the steps of:
    in a system comprising an outer tube having an open top end and a closed bottom end and containing a second fluid having a density at the minimum substantially equal to that of the first fluid but no greater than that of the particles, an inner tube having an open top end and an open bottom end, barrier means located within said inner tube for sealing said first fluid from said second fluid but adapted to be upwardly displaced into the inner tube thereby substantially eliminating its sealing capacity for permitting movement of the particles from the first fluid into the second fluid when a force substantially greater than 1G is applied, said inner tube adapted for insertion into the open end of said outer tube; putting said first fluid into said inner tube;
    inserting said inner tube into said outer tube;
    applying force to said particles directed toward the bottom of said outer tube whereby the barrier means is upwardly displaced into the inner tube and unsealed, and the particles are caused to move from said first fluid to said second fluid and to move through said second fluid to the bottom of said outer tube; and finally
    removing said inner tube, said first fluid and said second fluid.

2. The method as provided in claim 1 wherein the barrier means further comprises an orifice defining said bottom end having a diameter smaller than that of the inner tube and disposed within said orifice a material selected from the group consisting of synthetic film-forming materials, proteins, synthetic polymers and natural polymers.

3. The method as provided in claim 1 wherein said second fluid has at least one component adjusting the density of said second fluid selected from the group consisting of sodium chloride, glycine, sugars, serum albumin, natural polymers, natural copolymers, synthetic polymers, synthetic copolymers, dextran, and neutral polymers of sucrose; and wherein the second fluid so selected, does not, by itself, cause any substantial aggregation of the particles to be washed and collected.

4. The method as provided in claim 1 wherein said second fluid is serum albumin selected from the group consisting of animal serum albumin and human serum albumin.

5. A system for the washing and collection of particles contained in a first fluid comprising:
    (a) a first fluid containing particles to be washed;
    (b) an outer tube having an open top end and a closed bottom end and containing a second fluid having a density at the minimum substantially equal to that of the first fluid but, no greater than that of the particles;
    (c) an inner tube having an open top end and an open bottom end, containing said first fluid, and inserted into the open end of said outer tube; and
    (d) barrier means within said inner tube below the surface of said first fluid sealing said first fluid from said second fluid under forces of approximately 1G but adapted to be upwardly displaced into the inner tube thereby substantially eliminating its sealing capacity permitting movement of the particles from the first fluid into the second fluid when a force substantially greater than 1G is applied.

6. The system as described in claim 5 which further comprises means for supporting said inner tube within said outer tube.

7. A system for the washing and collection of particles contained in a first fluid comprising:
    (a) a first fluid containing particles to be washed;
    (b) a second fluid having a density at the minimum substantially equal to that of the first fluid but not greater than the density of the particles;
    (c) first means containing the second fluid, said first means having an open top end;
    (d) second means having an open top end and an open bottom end containing the first fluid which is inserted through the open top end of said first container means and into the second fluid, said second means having disposed at the bottom end thereof a barrier means sealingly containing and separately maintaining said first fluid from said second fluid and said barrier means adapted to be upwardly displaced into the second means thereby substantially eliminating its sealing capacity permitting movement of the particles from the first fluid into the second fluid when a force substantially greater than 1G is applied.

8. The system as described in claims 5 or 7 wherein the barrier means further comprises a substantially reduced diameter orifice defining said bottom end and dislocatably dispersed within said orifice a material selected from the group consisting of synthetic film forming materials, proteins, synthetic polymers, and natural polymers.

9. The system as described in claims 5 or 7 wherein said second fluid has at least one component adjusting the density of said second fluid selected from the group consisting of sodium chloride, glycine, sugars, serum albumin, natural polymers, natural copolymers, synthetic polymers, synthetic copolymers, dextran, and neutral polymers of sucrose; and wherein the second fluid so selected, does not, by itself, cause any substantial aggregation of the particles to be washed and collected.

10. The system as described in claims 5 or 7 wherein said second fluid is serum albumin selected from the group consisting of animal serum albumin and human serum albumin.

* * * * *